United States Patent [19]

Traiger et al.

[11] Patent Number: 4,564,355
[45] Date of Patent: Jan. 14, 1986

[54] METHOD AND APPARATUS FOR THE NON-INVASIVE EXAMINATION OF THE TOOTH-JAW STRUCTURE OF A PATIENT TO DETERMINE THE CHARACTERISTICS OF UNERUPTED TEETH AND TO CONTROL NUTRITIONAL INTAKE PURSUANT THERETO

[75] Inventors: Harry A. Traiger; Mark A. Traiger, both of New York, N.Y.

[73] Assignee: Dentonaut Lab, Ltd., New York, N.Y.

[21] Appl. No.: 569,459

[22] Filed: Jan. 9, 1984

[51] Int. Cl.⁴ ............................................. A61C 5/00
[52] U.S. Cl. .................................... 433/215; 128/633; 128/665
[58] Field of Search ................ 433/215; 128/633, 634, 128/644, 639, 660, 664, 665, 776, 777

[56] References Cited

U.S. PATENT DOCUMENTS

| | | | |
|---|---|---|---|
| 3,648,685 | 3/1972 | Hepp et al. | 128/665 |
| 4,084,582 | 4/1978 | Nigam | 128/660 |
| 4,167,331 | 9/1979 | Nielsen | 128/633 |
| 4,223,680 | 9/1980 | Jobsis | 128/633 |
| 4,380,240 | 4/1983 | Jobsis et al. | 128/633 |
| 4,467,812 | 8/1984 | Stoller | 128/664 |

Primary Examiner—John J. Wilson
Attorney, Agent, or Firm—Roberts, Spiecens and Cohen

[57] ABSTRACT

Apparatus for the measurement and analysis of tooth-jaw structures comprising a source of illumination, an optodetector and an integral linear displacement transducer. The source of illumination is used to transilluminate tooth-jaw structures while the optodetector receives light which has transilluminated the tooth-jaw structure. The linear displacement transducer provides a fast, accurate and precise size, distance and spatial measurement of structures comprising the tooth-jaw milieu. The system is particularly adapted for the intra-oral examination, measurement and analysis of unerupted teeth and their interdental spaces to detect a nutritional status that may exist which would impede the development of tooth-jaw concordance. A reiterative computer controlled process is employed to monitor and control preventive or remedial nutrition.

25 Claims, 10 Drawing Figures

FIG. 8A BLOCK DIAGRAM OF PREFERRED EMBODIMENT.

FIG. 9

METHOD AND APPARATUS FOR THE NON-INVASIVE EXAMINATION OF THE TOOTH-JAW STRUCTURE OF A PATIENT TO DETERMINE THE CHARACTERISTICS OF UNERUPTED TEETH AND TO CONTROL NUTRITIONAL INTAKE PURSUANT THERETO

FIELD OF THE INVENTION

This invention relates generally to dental measurement, and more particularly to a system for measuring, analyzing, and controlling the growth of primary dentition soon after birth by controlling nutritional intake. Such measurements are important and useful because the detection of incipient states of dental crowding (malocclusions) in early infancy permits the practitioner to offer appropriate therapeutic measures before the dental crowding progresses into a frank malocclusion.

BACKGROUND

Current methods for studying incipient states of dental crowding during early infancy are radiological and include the use of X-ray techniques thereby exposing neonates and young children to ionizing radiation. There is growing concern with adverse effects that may result from exposure to X-rays.

Once that danger is circumvented, the problem is to identify those infants who are at risk for developing handicapping malocculsion due to the size of jaw being too small for the size of the teeth, which shows up acutely when there is not enough spacing in the primary dentition for changeover to the larger permanent teeth, a condition known as incisor liability. Knowing that the width of the basal bone of the arch can only increase during the first several months after birth, the question is how to promote this growth of the jaw for an infant who is identified as being at risk for crowding. Once the infant's genetic potential for growth is determined by measuring an unerupted primary tooth it becomes possible to apply nutritional means for reaching the genetically correct amount of growth; however, it is necessary to control and periodically modify the calorie intake based on changing amounts of growth and the time constraint for arch width increase. It is also necessary to provide a process for automatically controlling the feeding of approximately forty percent of the infants who need large amounts of nutrients due to a severe risk for crowding.

A significant clinical feeding problem addressed by the present invention relates to the hospital care of premature infants. After the acute crisis subsides with intensive feeding measures, the attending physician needs a quantitative criterion in order to set a desirable caloric flow rate for a particular premature infant.

Another important practical problem for the physician is to utilize an acceptable criterion that will convince infant caregivers to follow professional feeding orders rather than parental zeal or prejudices, in order to avoid infant overfeeding (obesity) or underfeeding problems. Such a criterion is inherent in the invention.

The term "tooth-jaw structure" is intended to refer to the general structure of the patient inclusive of the gums. It is to be appreciated that it is the gums which are irradiated to provide outline of the unerupted teeth present in the gums.

SUMMARY OF THE INVENTION

It is therfore an important object of this invention to provide apparatus for measuring and analyzing the growth and development of tooth-jaw structures which does not employ X-rays or other ionizing radiation of film.

In view of the foregoing, transillumination of the tooth-jaw structures with non-ionizing photons and subsequent detection of those photons which have transilluminated the tooth-jaw structures is an important object of this invention.

Those skilled in the art will understand that photon sources for transillumination should be of sufficient intensity to penetrate and traverse the anatomical portion being studied. This may be provided by several means. An incandescent lamp may provide such photons. It will be understood by those skilled in the art that a convenient means of using an incandescent light source is to use a reflector-type lamp housed in a light beam projector. A fiber optic type of light beam projector will also provide this function. The lamp may be used with a focusing lens with or without said fiber optic element. Yet another photon source may be a light emitting diode. The advantage of this light source is its low voltge and current requirements. A light emitting diode of the infrared type may be advantageous since infrared photons can provide a good contrast between tooth jaw or other structures. Infrared light emitting diodes are also advantageous because they are detectable by photodetectors which respond principally in the infrared region of the spectrum thereby limiting the adverse effects of ambient light. Since a high intensity light source is useful in transilluminating methods, the use of a laser photon source is of particular utility due to its high intensity. Furthermore, such devices are available which emit in the infrared region and are of the light emitting diode type thereby providing high intensity, improved contrast, low voltage and current power requirements and the aforementioned immunity to ambient light of a system employing an infrared light source with a matched photodetector.

Another object of this invention is to provide apparatus for measuring the size, space and distance between and among tooth-jaw structures. This is provided by the combined use of a photodetector and linear displacement transducer in integral conjunction with the aforementioned light source and beam projector. The photodetector senses photons which have transilluminated the anatomical portion of interest. In the case of tooth-jaw structures under transillumination, a tooth, either unerupted or erupted will block the transmission of light from the integral light beam source. The photodetector will sense the change of intensity of transilluminating photons. The photodetector in the preferred embodiment is a phototransistor, however, it will be understood by those skilled in the art that a variety of photodetectors may be used within the invention. These include but are not limited to photodiodes, photomultipliers, photoresistors, photovoltaic devices, vidicon tubes and charge coupled devices.

Nuclear magnetic resonance can be employed instead of light. This involves applying a fixed magnetic field to the target tissue area, along with an oscillating electromagnetic field from a miniature radio transmitter and a miniature radio receiver to detect the re-radiation from said body tissues. The position of said radio receiver would be transduced to provide the desired tooth width and interdental spacing measurements.

In a presented embodiment, the integral linear displacement transducer is a linear output Hall effect device. This magnetically sensitive device is used in conjunction with a magnet to provide a change in output as a function of distance from the magnet which serves the dual function of providing a magnetic field for the Hall sensor, and a datum or reference in determining the distance of the integral photodetector from the magnet. The magnet is of the rare earth type in general and more specifically, samarium cobalt. This type of magnet has a highly stable field strength and a high energy product providing an accurately measureable field throughout the distances needed to perform the measurement. Other magnets may be employed within the scope of the invention.

A further object of this invention is to provide a system of the above type which is electronically isolated from the practitioner and patient thereby avoiding the hazard of electrical shock. This may be accomplished by the use of optoisolators and insulated shielded wiring.

A further object of the invention is to provide a system of the above type which includes means for processing the outputs of the linear displacement transducer and the photodetector such that the practitioner can be provided with the desired measurements. This may be accomplished by feeding said signals into a subsystem comprising sample and hold amplifiers, analog to digital converters, display electronics, storage electronics, signal processing electronics and a power supply to energize said signal acquisition and processing electronics. The above function can be performed by a variety of means including but not limited to such data translation methods as data acquisition modules, comprising multiplexing circuitry, sample and hold amplification circuitry, analog to digital conversion circuitry and interface circuitry for subsequent processing by a computer system.

The computer system may be microprocessor based, microcomputer based, minicomputer based or mainframe computer based. Such data acquisition and signal processing subsystems may include signal conditioning circuitry and software to achieve the desired analysis and result. Such circuitry may include but is not limited to analog multipliers, true RMS converters, active filters, digital filters, digital signal processing devices such as Texas Instruments TMS 320, TRW TD 1023J, Intel 2920, American Microsystems S 2811 and NEC 7720.

It will be understood by those skilled in the art that the software to work in conjunction with data acquisition, conditioning and processing circuitry and subsystems may reside in programmable read-only-memory devices, erasable programmable read-only-memory devices, the aforementioned digital signal processing devices, magnetic tape or disk drive systems or other data storage devices or systems. Algorithms for such processing subsystems may include but are not limited to image processing methods exemplified by skeletization, inverse skeletization, feature extraction, content addressing, look-up table, associative addressing, spectrum analysis, fast Fourier transforms, inverse fast Fourier transforms, convolution integration and inverse convolution integration. Such algorithms may be implemented on the aforementioned digital signal processing devices upon their manufacture or fabrication thereby made available as an integral feature of said devices.

Another important object of this invention is to perform the analysis of data acquired during and after the use of the above system by means other than those disclosed and the aforementioned methods are merely examples of the implementation of analysis and are not to be construed as limitations upon the several aforementioned methods of tooth-jaw analysis.

In accordance with the above, the invention provides for apparatus for the non-invasive examination of the tooth-jaw structure of a patient to determine the characteristics of unerupted teeth in said structure wherein the apparatus comprises means for producing a beam of energy outside the X-ray region and within the region of infrared, visible light or ultrasound. The beam producing means is mounted on a support means for positioning the beam producing means such that the beam of energy therefrom strikes the tooth-jaw structure and undergoes modification depending on the presence of unerupted teeth and their size and position in the tooth-jaw structure. A receiver means is mounted on the support means for receiving the beam of energy after striking the tooth-jaw structure to produce the characteristics of unerupted teeth in said structure. Coupled to the receiver means is a locator means for producing an indication of the location of the receiver means such that the characteristics of the unerupted teeth are related spatially.

Preferably, the support means comprises a portable hand-held unit adapted for being placed adjacent to the tooth-jaw structure.

In a preferred embodiment, the beam producing means comprises a light source for transilluminating the jaw structure, the receiver means is a photodetector and the locator means is a linear displacement transducer.

The invention is also concerned with a method of determining the growth of primary dentition in the tooth-jaw development process without the use of X-rays and the method comprises irradiating the tooth-jaw structure, in the course of development thereof by a beam of non-ionizing energy from a non-X-ray source. In further accordance with the method of the invention, the beam of energy is received after irradiation of the tooth-jaw structure by the beam and information indicating the presence or absence of unerupted teeth in the gums of the tooth-jaw structure and the size, spacing and location of said unerupted teeth are produced whereby the growth of primary dentition can be determined.

The method of the invention also contemplates controlling the caloric intake of the patient in accordance with the determined values of the size, spacing, and location of the unerupted teeth so that the growth of primary dentition is regulated to provide desired interdental spacing and consequent tooth-jaw concordance.

DETAILED DESCRIPTIONS

The invention will be described in detail hereafter with reference to a system for measuring, analyzing, predicting, and controlling nutrition for preventing or reducing dental crowding and promoting desirable infant dental growth. More particularly, this is done through a computer or microprocessor based system that is specifically programmed according to this invention. One aspect of the invention is to determine to what degree, if any, tested infants are at risk to develop malocculsion due to malnutrition. This can be related to the marked decrease in food intake that takes place, generally, at two months of age which is a crucial time when the infant's jaw is capable of favorable anterior growth patterns.

The invention considers this reduction in food intake to be a prime environmental factor in the development of tooth-arch discrepancies in susceptible infants. An infant's food consumption requirements for concordant growth, as defined later herein, can be assessed from tooth size and the genetic potential for growth that such size variations intrinsically represent. In use, the first examination of the infant by means of the invention establishes and enters age and body length into the computer, and sensors will measure tooth width and interdental spacing from illuminated gums and also provide this as an input to the computer. In follow up examinations, it is unnecessary to enter the infant's age because a real-time clock calendar will be incorporated in the computer. Furthermore, in follow up examinations it is optional to measure tooth width since this does not change once the tooth is fully calcified, and, in connection with the upper primary central incisor tooth, this occurs prior to two months of age. It is also optional to measure body length after its initial entry, since an infant's growth can be assessed by measuring the amount of interdental spacing with the oral sensors.

Another aspect of the invention is to use the information from the computer analysis, described subsequently, for determining the infant's degree of risk for developing crowding, in order to control the flow rate of liquid nutrients through an infant feeding tube, which may be administered by a physcan nasogastrically, enternally, or parenterally. The control of the flow rate may be accomplished by an Oriel precision motorized micrometer or other suitable computer controlled means known to those skilled in the art. Alternatively, in situations where the infant's growth discrepancy is small, the computer can produce schedules for breast or bottle feeding.

Still another objective of this invention is to provide a multi-task computer capable of simultaneously monitoring and controlling the feeding of a number of infants through a local area network controller.

This invention involves the evaluation of dental growth concordance and the nutritional recommendations for correcting nonconcordance which are arrived at taking into account the following factors incorporated into a computer program of the present type:

1. The body length of the infant is measured and based on the infant's age, a body length percentile is determined on the basis of growth percentile values from standard tables that have been programmed into the computer as look-up tables.

2. The tooth width of the infant is measured and this value in millimeters is multiplied by a factor K to obtain a theoretical body length percentile. The factor K is the ratio of the maximum body length percentile of a given population to the maximum tooth width of the population and the value K may vary for different populations. A typical value of K may be in the range between 10 and 15.

3. The tooth-jaw concordance is determined by subtracting the actual body length percentile from the theoretical body length percentile to obtain length percentile discrepancy. In the small fraction of cases where the actual body length percentile is equal to or exceeds the theoretical body length percentile, no change in the calorie intake is needed, however, follow up exams may be useful. In general, the theoretical body length percentile is the maximum growth percentile that can be reached; if it is not reached, varying degrees of dental crowding will probably result.

4. It has been found that this discrepancy is related to interdental spacing by the following empirical regression equation:

$$\text{Interdental Spacing mm.} = -0.4546 \times \frac{\text{percentile Discrepancy}}{100} + 0.4407$$

The empirical equation is additive since tooth-jaw concordance or lack thereof (i.e. crowding) is adequately represented by the body length percentile discrepancy factor and since interdental spacing may be measured directly with the oral status measuring sensors of this invention.

5. For a particular age and based on a theoretical body length percentile, a theoretical daily calorie intake can be obtained from various look-up tables programmed in the computer. In order to determine the remedial daily calorie intake when catch-up growth is indicated, the invention contemplates that to the theoretical body length percentile is added the discrepancy factor i.e., the body length percentile discrepancy. As a consequence, a remedial daily calorie intake is obtained.

6. The position of the motorized micrometer, or other means, required to provide the desired nutrient flow rate corresponding to the calculated theroretical daily calorie intake, or an intermediate value, is adjusted automatically by means described or known to those skilled in this art.

Although the tooth width and, hence, theoretical body length percentile does not change as a particular infant gets older, and although actual body length percentile normally does not change, it is expected that when a corrective regimen of calorie intake and necessary care is supplied to an infant who is below his or her theoretical body length percentile and, thus, at risk for developing tooth crowding, the infant's actual body length percentile will increase towards the theoretical standing and simultaneously, the growth of the jaw (arch width) will increase to reduce the degree of crowding until approximately six months after birth.

7. Hence, it is desirable to follow the progress of the infant on a serial basis as often as may be deemed necessary and to determine the reduction in body length percentile discrepancy and the reduction in tooth crowding. At each age, a new corrected calorie intake will be calculated and the regimen can be modified to find a "critical path" to the correct calorie intake and to the ideal amount of interdental spacing estimated to be 0.44 mm. plus or minus $S_b$ obtained from the intercept of the "best fit" line represented by the empirical regression equation. The critical path method takes the time factor into account, which is important because the arch width can only increase until approximately six months after birth. Nutrition and nutritionally related means can only be effective in reducing crowding during this critical period.

8. A further regression equation which is useful is:

$$\frac{\text{Interdental spacing}}{\text{Tooth Width}} = \frac{-0.0668 \times \text{percentile Discrepancy}}{100} + 0.0684.$$

9. When the invention is to be employed for premature infants, the width of a transilluminated tooth at birth is determined with oral sensors or analyzers. The computer's operating subprogram multiplies the tooth width value by the reciprocal of a known fraction representing the degree of completed crown formation at birth. From this the system determines caloric values, and sets the flow rates of feeding tubes accordingly to achieve concordant dental growth for these premature infants.

10. Since the invention is based on effecting flow rates or feeding schedules for infants, it should circumvent the zeal or prejudices of infant caregivers that give rise to health problems related to obesity or dehydration.

In all operations of the invention, the attending physician or dentist are the final arbiters, and they are professionally responsible for using their judgment to accept, modify, or reject the information or settings that the apparatus produces.

Figure 1:
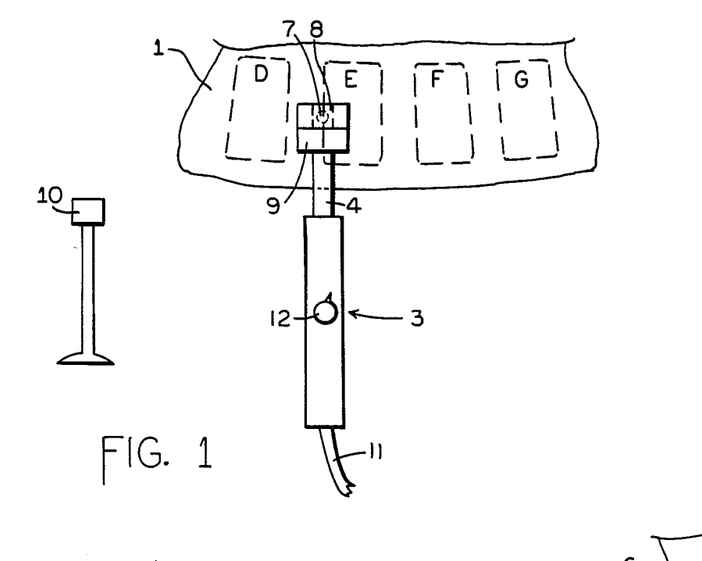
FIG. 1 is a front view diagrammatically illustrating the apparatus of the invention of use in the irradiation of tooth-jaw structure.
Figure 2:
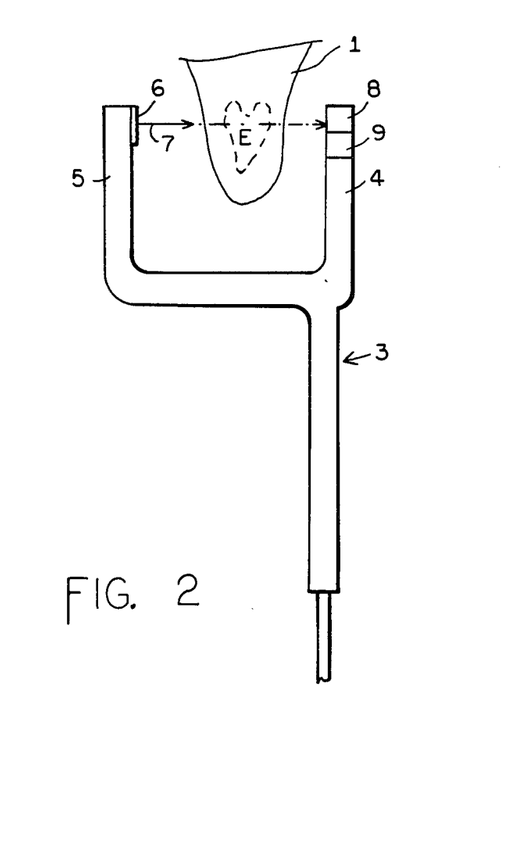
FIG. 2 is a side elevational view of the structure shown in FIG. 1.

FIGS. 1 and 2 show a simplified embodiment of an analyzer or sensor for measuring the width of unerupted teeth and interdental spacing without the use of X-rays and in these figures the tooth-jaw structure is designated D,E,F,G according to American Dental Association nomenclature.

Figure 9:
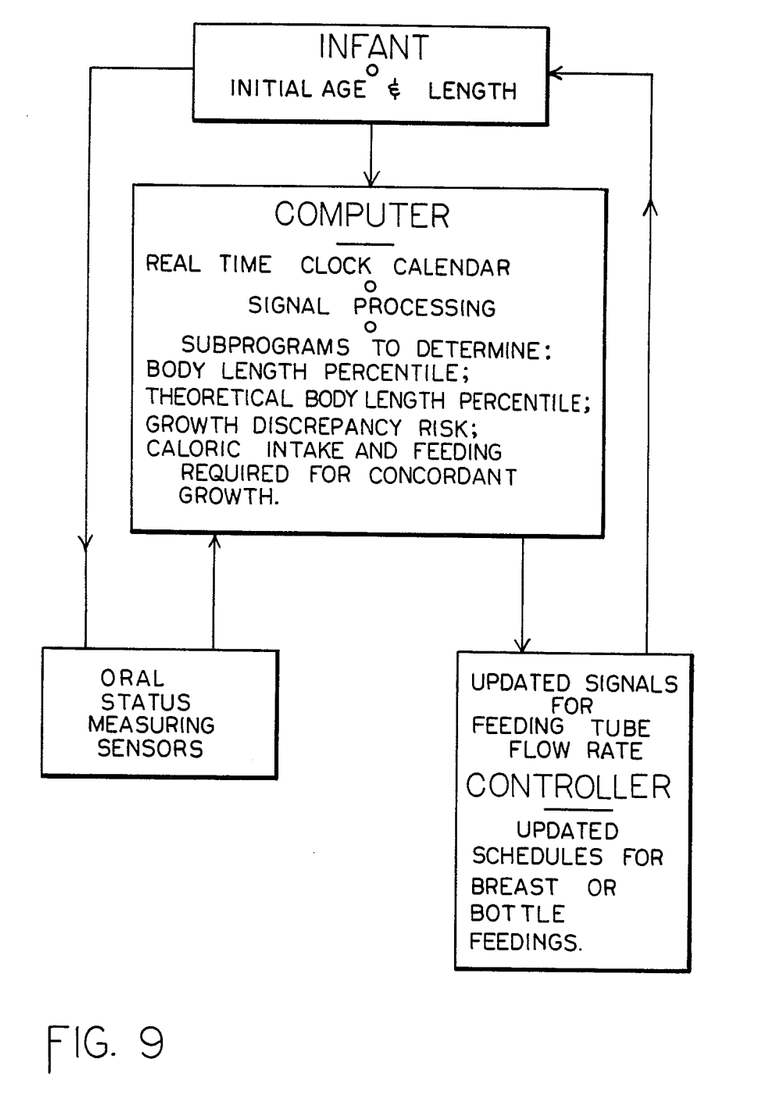
FIG. 9 is a schematic illustration of a system for achieving concordant infant dental growth.

FIG. 9 illustrates schematically a system showing the flow of data and control signals. The system operates according to a feedback process as will be described later.

The analyzer comprises a portable hand-held unit 3 adapted for being placed adjacent to the tooth-jaw structure 1. More particularly, the hand-held unit 3 comprises a front branch 4 and a rear branch 5 adapted to straddle the tooth-jaw structure 1 as seen in FIG. 2. The branch 4 is disposed facially i.e. externally of the tooth-jaw structure while branch 5 is disposed palatally i.e. within the mouth facing the interior surface of the tooth-jaw structure 1. Mounted on the branch 5 of the unit 3 is a light source 6 for transilluminating the tooth-jaw structure. The light source produces a beam of energy which is outside the X-ray region so as not to expose the infant under examination to ionizing radiation. The beam of energy is within the region of infrared, visible light or ultrasonic wavelengths. As diagrammatically illustrated in FIG. 2, the beam of energy produced by the light source is indicated by numeral 7 and strikes a photodetector 8 mounted on the unit 4. The photodetector serves as a receiver means for receiving the beam of energy after it has undergone modification upon passing through the tooth-jaw structure depending upon the presence of unerupted teeth and their size and position in the tooth-jaw structure. The information received by the photodetector is utilized to produce the characteristics of unerupted teeth in the tooth-jaw structure as will be explained later.

Additionally supported on the branch 4 is a locator means 9 which is in fixed relation to the photodetector 8. The locator means serves to produce an indication of the location of the receiver means such that the characteristics of the unerupted teeth can be related spatially. In particular locator means 9 is constituted as a linear distance or displacement transducer as will be explained hereafter.

The linear displacement transducer is a conventional linear output Hall effect device as, for example, found in the commercial market as exemplified by the Honeywell-Microswitch 9SS (Lohet TM). This is a magnetically sensitive device which employs a magnet 10 which establishes a field so that the locator 9 provides a change in output as a function of distance from the magnet. Hence, the magnet serves the dual function of providing a magnetic field for the locator or sensor and a datum for reference in determining the distance of the photodetector 8 from the magnet. As is well known, the magnet 10 can be of the rare earth type and, particularly, a samarium cobalt magnet. This type of magnet has a highly stable field strength and a high energy product providing an accurately measurable field throughout the distances needed to perform the function of the analyzer of the invention.

The unit 3 can be battery powered, in which case it will be self-contained and fully portable without any cables of any sort. The unit can also be externally powered, for example, through a cable 11 connected to a suitable power source. A switch 12 can be provided on the unit 3 with separate positions for energizing the optic source alone and the optic source as well as the linear displacement transducer.

Figure 3:
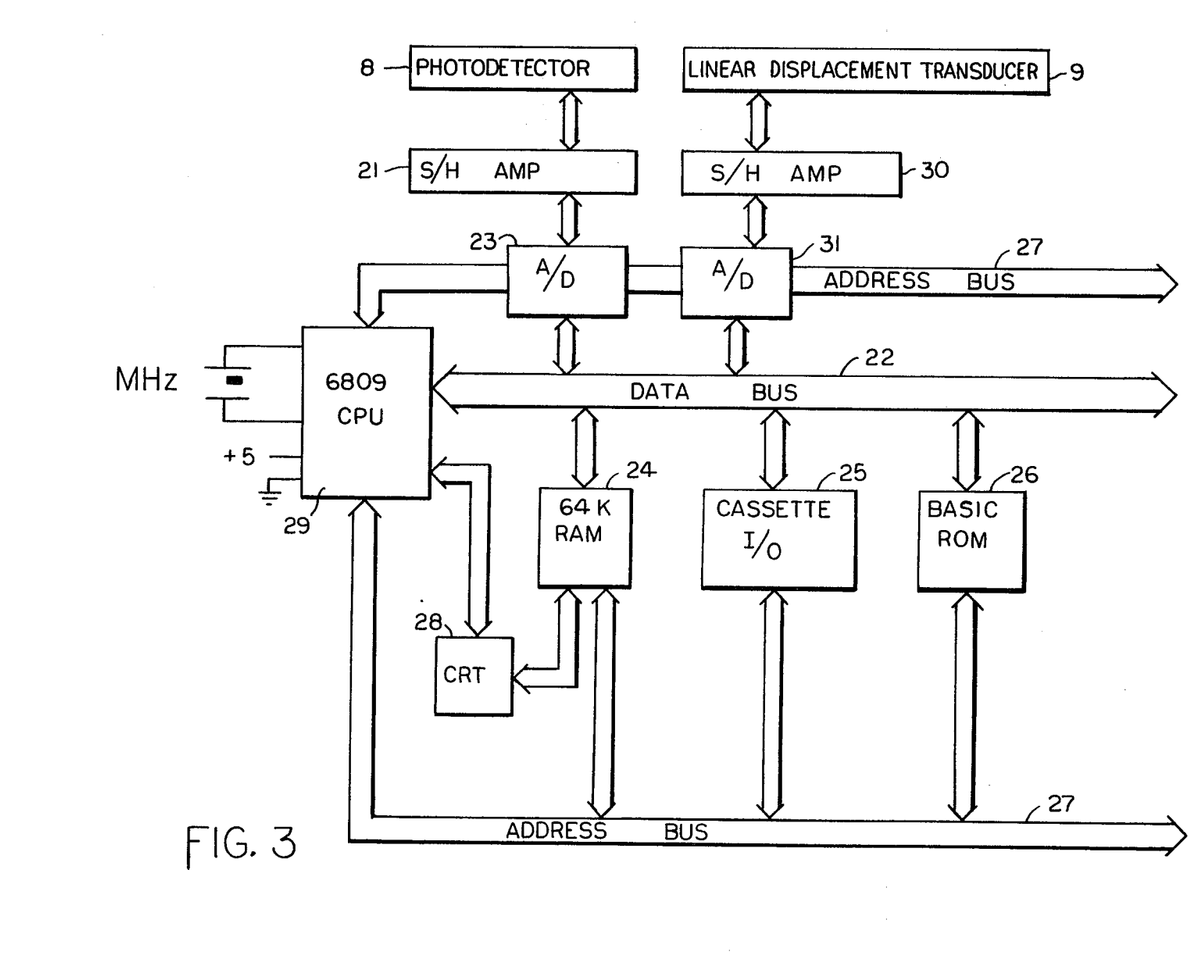
FIG. 3 is a diagrammatic illustration of an operating system utilized with the apparatus of the invention.

In operation, the unit 3 is displaced along the tooth-jaw structure and the light beam 7 traverses the tooth-jaw structure and undergoes alteration in accordance with the size and position of the unerupted teeth D,E,F,G. An operating system 13 is provided as shown in FIG. 3. The receiving means 8 comprises a photodiode, such as a Vactec VTB9413B, which is mounted on a movable linear displacement transducer 9, such as a Microswitch 9SS Hall-effect device. The CPU 29 is an 8 bit microprocessor, for example, a Motorola 6809, which is loaded with appropriate data processing software under control of the Basic interpreter stored in read only memory 26 through the cassette I/O port 25, directing the processing of the signals from transducers 8 and 9 into meaningful tooth width and spacing measurements. The signals from the receiving means 8 and the linear transducer 9 are fed into sample/hold amplifiers 21 and 30 which supply acceptable signal characteristics to the A/D converters 23 and 31 each having 12 bit resolution. The digitized output signals from the A/D converters are fed into the CPU 29 across a dedicated address space 27 on the data bus 22. The CPU 29 in turn processes the outputs as follows. The digitized A/D output values are stored in random access memory 24, under software control, the CPU subtracts the values which it has been determined correspond to the ends of the unerupted teeth using standard signal processing techniques known to those skilled in the art. The resulting measurements of tooth width and interdental spacing are displayed on the operator CRT 28.

Figure 4:
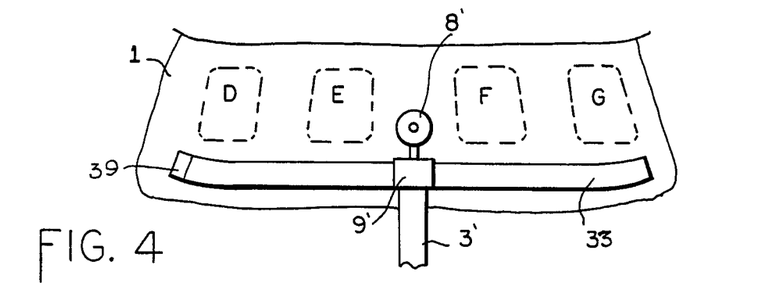
FIG. 4 shows a front view of a modified structure.
Figure 5:
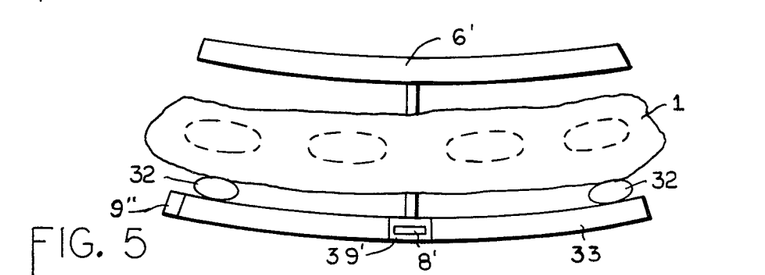
FIG. 5 is a plan view from above of the structure in FIG. 4, showing an interchange in the position of two means.

Many variations of the analyzer are within the skill of those with knowledge in this art and, in particular, numerous embodiments of different linear transducers are possible. By way of example, reference is made to FIGS. 4 and 5 which show the provision of a unit 3' which carries a photodetector 8' and transducer 9' for sliding movement along a curved support 33. The transducer works in accordance with the Hall effect, but it is modified as shown in FIGS. 4 and 5 to obviate the need for a separate magnet 10 positioned independently of the apparatus. In FIG. 4, the transducer 9' travels along a curved support 33 to correspond to the dental arch and forms a magnetopot with the magnet 39. In FIG. 5, the photodetector 8' is integrally mounted on the magnet 39'. The magnet 39' can be a rare earth magnet or an electromagnet and, preferably, is encapsulated in plastic. The sensor or transducer is fixed to the support 33 as shown at 9" and it produces signals in relation to the magnitude of displacement of the magnet 39' along the support. The signals from sensor 9" are digitized and are fed to the storage 24 in the embodiment of the operating system as shown in FIG. 3. The light source 6' is also curved to conform to the dental arch.

In operation, the magnet 39' is displaced along the support 33 and the sensor 9" produces output signals related to the position of the magnet 39' from the sensor 9". The detector 8' receives the light beam after passage through the tooth-jaw structure 1 and these are fed to sample/hold amplifier 21 in the system shown in FIG. 3. The output display gives values of the tooth width and the interdental spacing after data processing.

In FIGS. 4 and 5, the Hall effect device and magnet interrelate in a head-on mode. The Hall effect device may also be configured in a slide-by mode in relation to the magnet. In other variations of these embodiments, more than one magnet may be employed with a sensor or more than one Hall effect device may be used with a magnet. In order to secure the unit in a stationary position against the jaw structure, soft positioners 32 can be provided at the ends of the support 33 in order to hold the unit in a stationary bearing position against the tooth-jaw structure 1. As an alternate arrangement, the unit 3' can be secured in fixed relation in respect to the infant under test in any other suitable fashion.

Figure 6:
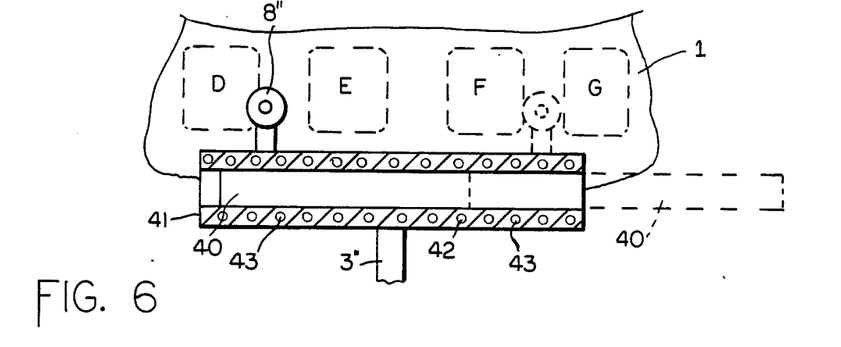
FIG. 6 is a side view partly in section showing a modification of the structure.
Figure 7:
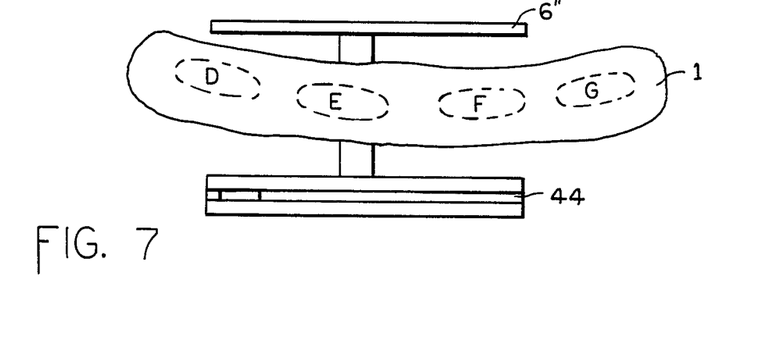
FIG. 7 is a plan view from above of the structure in FIG. 6.

FIGS. 6 and 7 show another embodiment of a linear transducer and this operates to produce an electrical output proportional to the displacement of a movable core 40 within a housing 41 containing a primary coil 42 and two secondary coils 43 symmetrically placed with respect to the primary coil 42. The core 40 serves as a free moving magnetic core inside the coil assembly to provide a path for the magnetic flux linking the coils. Therefore, the net output of the transducer is the difference between the voltages induced in the secondary coils which is zero when the core is at the center or null position. When the core is moved from the null position, the induced voltage in the coil toward which the core is moved increases while the induced voltage in the opposite coil decreases. This action produces a differential voltage output that varies linearly with changes in core position. The phase of this output voltage changes abruptly by 180° as the core is moved from one side of the null position to the other.

In operation, the displacement of the core 40 therefore can be an indication of the linear displacement of the transducer. The photodetector 8" is secured to the core and travels within a slot 44 in the housing. As an alternative to the formation of a slot, the photodetector 8" could be externally connected to the core to either of the opened ends of the housing whereby the housing and its coils can remain intact. The optical source 6" is linearly arranged parallel to the transducer composed of the core 40 and housing 41. In operation, the photodetector 8" is displaced along the housing which is, itself, integrated with the unit 3" so that the photodetector 8" will receive the beam of light from the light source (in this case, a plane of light) after it has passed through the tooth-jaw structure 1 and has been altered by the unerupted teeth D,E,F,G. The signals from the linear transducer are fed to the operating system shown in FIG. 3 and an output will be produced to indicate the values of the width of the unerupted teeth and the tooth spacing after data processing.

Such a transducer as shown in FIGS. 6 and 7 is currently available from the Schaevitz Company and is designated as an LVDT linear transducer. Advantages of the use of this transducer in its standard forms are that the photodetector can adjustably trace the transillumined contour outline of the gums and relative positioning of the portions of the unerupted teeth of interest, extremely high linearity, and long part life.

Figure 8:
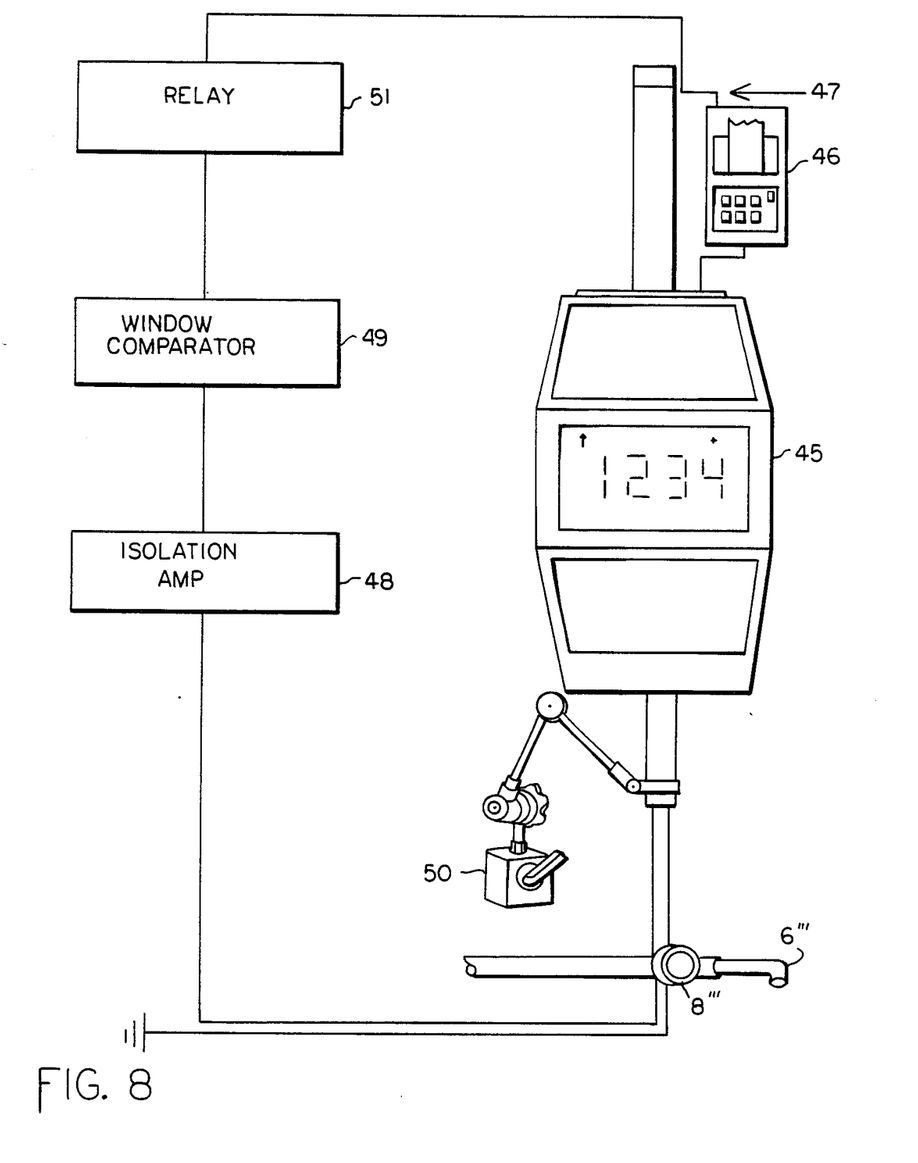
FIG. 8 is a block diagram of another operating system according to the invention.
Figure 8A:
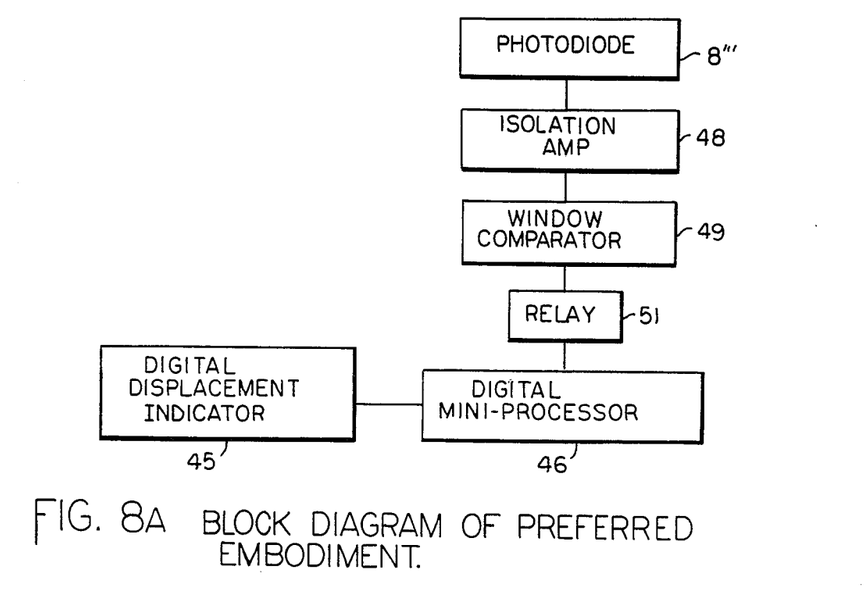
FIG. 8A is a more detailed schematic illustration of the system of FIG. 8.

A further embodiment is shown in FIG. 8 and comprises a measuring system which includes a Mitutyo series 543 Digimatic Indicator 45 which measures displacement by a photoelectric encoder. The indicator 45 produces a digital output which is fed to a Mitutoyo series 264 Digimatic Mini-Processor 46 having a remote switch jack 47 for initiating a printing operation. The measurement of tooth width and interdental spacing is accomplished by having an integral light source 6''' preferably of the fiber optic autoclavable type, and an integral photodetector 8''' which is preferably a Vactec VTB 9413B blue-enhanced ultra-high dark resistance photodiode. The signal from said photodiode is connected to an isolation amplifier transimpedance circuit using a suitable isolation amplifier 48. The output voltage of this circuit is connected to a window comparator 49 preferably a Burr-Brown model 4115/04 the "go" output of which is connected to the coil of a suitable relay 51 having normally open contacts and in turn connected to the remote switch jack 47 of Mini-Processor 46. By setting the upper and lower cutoffs of the window comparator 49, the positions of the tooth edges are printed out on the Mini-Processor 46 since the anatomical crest at the side of a tooth is thinner than the rest of the tooth. A brief pause in advancing the photodetector 8''' may be needed to allow the printer of the Mini-Processor 46 sufficient time to reset itself between printing out values. The desired measurements are obtained by manually subtracting each adjoining number, or the subtractions could be obtained automatically by interfacing the output of the Digimatic Indicator 45 and window comparator 49 to a suitably programmed computer. The association of the calculated differences with the corresponding dimensions of the teeth and interdental spaces are easily deduced by the operator based on the sequence in which they were scanned and by the fact that the interdental spaces are much smaller than the teeth, or if the computer were informed of the scanning sequence it would make the assignments under program control. An advantage of this embodiment is that no zero position need be set for the distance measurements and no distance calibration is required. Furthermore, aside from the need to scan at the level of the widest portion of each tooth of interest, the operator is relieved from performing manual measurements which require careful alignment. In operation, suitable power supplies are provided, as needed; potentiometers can be used to set the upper and lower voltage cutoffs needed to detect the edge of a tooth of a particular infant being examined.

It should be clear that the above technique requires that the body of the Digimatic Indicator 45 must be stationary with respect to the infant's upper gums. This may be accomplished by placing the Digimatic Indicator 45 in a Mitutoyo 213–103P Universal Magnetic Stand 50 and the subject's head may be stabilized with straps from an infant restraining board and the head may be further immobilized between the palms of the hands by an assistant, who may at the same time deflect the upper lip away from the gums with two fingers at the corners of the mouth.

Another variation of the above embodiment of the invention is to connect a Mitutoyo series 542–323 linear gage to a Mitutoyo 332–121 Optoeye Al that has an integral light source and photodetector mounted on the spindle of the linear gage. A suitable power source is provided and the above means for stabilizing components and the subject are effected to avoid the effects of unwanted movements upon the measurements.

Referring again to FIG. 9 therein is seen a feedback system controlling infant feeding on the basis of input data and control signals. As shown in FIG. 9, the infant is monitored initially for age and body length and these values are fed to the computer which incorporates a real time clock calendar and subprograms of parameters previously described in detail to determine
body length percentile
theoretical length percentile
growth discrepancy risk
feeding requirement for concordant growth A controller is connected to the computer for receiving signals therefrom and the controller can directly regulate the feeding of the infant by controlling the flow rate in a feeding tube connected to the infant or the controller can provide updated schedules for manual feeding of the infant by breast or bottle feeding.

In this way the caloric intake of the infant can be controlled in accordance with the parameters furnished by the sensors or analyzers so that the growth of primary dentition is regulated to provide desired interdental spacing or tooth-jaw concordance.

Although the invention has been described in relation to a number of embodiments thereof, it will become apparent to those skilled in the art that numerous modifications and variations can be made within the scope and spirit of the invention as defined in the attached claims.

For example, in connection with the preferred embodiments, the output of a custom-match window comparator may directly act as a power source to drive the mini processor/printer, whose remote switch is kept normally closed, thus eliminating the need for a relay and a separate power supply for the mini/processor printer.

What is claimed is:

1. Apparatus for the non-invasive examination of the tooth-jaw structure of a patient to determine the characteristics of unerupted teeth in said structure, said apparatus comprising means for producing a beam of energy support means for said beam producing means for positioning the same such that the beam of energy strikes the tooth-jaw structure and undergoes modification depending on the presence of unerupted teeth and their size and position in the tooth-jaw structure, receiver means on said support means for receiving the beam of energy after striking the tooth-jaw structure or after re-radiation by the tooth-jaw structure to produce the characteristics of unerupted teeth in said structure, and locator means coupled to said receiver means for producing an indication of the location of said receiver means such that the characteristics of the unerupted teeth are related spatially.

2. Apparatus as claimed in claim 1, wherein said support means comprises a portable hand-held unit adapted for being placed adjacent to said tooth-jaw structure.

3. Apparatus as claimed in claim 1, wherein said beam producing means comprises a light source for transilluminating the tooth-jaw structure, said light source and receiver means being spaced apart on said support means to straddle the gums of the tooth-jaw structure of the patient.

4. Apparatus as claimed in claim 3 wherein said support means comprises a portable hand-held unit.

5. Apparatus as claimed in claim 4 wherein said beam producing means, receiver means, and locator means are secured to said unit.

6. Apparatus as claimed in claim 5 comprising means for establishing a reference datum location and wherein said locator means provides indication of the linear distance of said receiver means from said datum position.

7. Apparatus as claimed in claim 3 wherein said beam producing means is positioned on said support means for insertion into the mouth cavity of the patient behind the tooth-jaw structure with said receiver means and locator means positioned in front of the tooth-jaw structure.

8. Apparatus as claimed in claim 1 further comprising processing means for receiving the output of said receiver means and said locator means to produce indication of the size and spacing of unerupted teeth.

9. Apparatus as claimed in claim 1 comprising means for producing a magnetic field which in combination with said beam of energy produces magnetic resonance.

10. Apparatus as claimed in claim 1 wherein said beam of energy is electromagnetic.

11. Apparatus as claimed in claim 10 wherein said electromagnetic beam of energy has a wavelength in the field including infra-red and visible light.

12. Apparatus as claimed in claim 1 wherein said beam of energy is ultrasonic sound.

13. Apparatus for the non-invasive examination of a selected anatomical structure of a patient without the use of ionizing radiation such as X-rays, said apparatus comprising a support adapted for placement adjacent to a selected anatomical structure of a patient to be examined, beam producing means on said support for producing a beam of energy of non-ionizing radiation outside the X-ray region for impingement on the selected anatomical structure, receiver means on said support in fixed relation to said beam producing means for receiving said beam of energy after impingement thereof on said selected anatomical structure or after re-radiation by said selected anatomical structure, locator means on said support in relation to said beam producing means and said receiver means for indicating the spatial location of said receiver means, and processing means for receiving outputs from said receiver means and locator means to provide information concerning said selected anatomical structure.

14. Apparatus as claimed in claim 13, wherein said support means comprises a portable hand-held unit adapted for being placed adjacent to said selected anatomical structure.

15. Apparatus as claimed in claim 14, wherein said beam producing means, receiver means, and locator means are secured to said unit.

16. Apparatus as claimed in claim 13, wherein said beam producing means comprises a light source and said receiver means comprising a photodetector.

17. Apparatus as claimed in claim 16, wherein said light source and photodetector are spaced apart on said support means for introduction of the anatomical structure therebetween.

18. Apparatus as claimed in claim 13, comprising means for establishing a reference datum location and wherein said locator means provides indication of the linear distance of said receiver means from said datum position.

19. A method of determining the growth of primary dentition in the tooth-jaw development process without the use of X-rays, said method comprising irradiating the tooth-jaw structure, in the course of development thereof, by a beam of non-ionizing energy from a non-X-ray source, receiving said beam of energy after irradiation of the tooth-jaw structure by said beam or after re-radiation by the tooth-jaw structure, and producing information indicating the presence or absence of unerupted teeth in the gums of the tooth-jaw structure and the size, spacing and location of said unerupted teeth whereby the growth of primary dentition can be determined.

20. A method as claimed in claim 19, wherein the information concerning the size, spacing and location of the unerupted teeth is produced by determining the position of the received beam of energy after irradiation of the tooth-jaw structure.

21. A method for determining the growth concordance of the primary dentition and the calorie intake necessary to achieve tooth-jaw concordance or favorable interdental spacing, said method comprising producing a beam of energy from a non-X-ray source, applying said beam to the gums of a patient containing unerupted teeth, receiving said beam of energy after it strikes the gums, producing information indicating the presence or absence of unerupted teeth in the gums, and the size, spacing, and location of said unerupted teeth, determining actual body length percentile, body length percentile discrepancy, and concordant calorie intake based on age and theoretical body length percentile of the patient, and monitoring these parameters on a serial basis with modification of the caloric intake of the patient to effect an ideal amount of interdental spacing.

22. A method as claimed in claim 21, wherein the information concerning the size, spacing, and location of the unerupted teeth is produced by determining the position of the received beam of energy after it strikes the gums containing the unerupted teeth.

23. A method of controlling the growth of primary dentition of a patient in the tooth-jaw development process, said method comprising irradiating the tooth-jaw structure in the course of development thereof, by a beam of energy from an energy source, receiving said beam of energy after irradiation of the tooth-jaw structure by said beam or after re-radiation by the tooth-jaw structure, determining the presence or absence of unerupted teeth in the gums of the tooth-jaw structure and parameters including the size, spacing and location of said unerupted teeth and controlling the caloric intake of the patient in accordance with the determined parameters so that the growth of primary dentition is regulated to provide desired interdental spacing.

24. A method as claimed in claim 23, wherein the parameters including the size, spacing and location of the unerupted teeth are determined by detecting the position of the received beam of energy after irradiation of the tooth-jaw structure.

25. A method for determining the growth concordance of the primary dentition and the calorie intake necessary to achieve tooth-jaw concordance or favorable interdental spacing, said method comprising producing a beam of energy from an energy source, applying said beam to the gums of a patient containing unerupted teeth, receiving said beam of energy after it strikes the gums, producing information indicating the presence or absence of unerupted teeth in the gums, and the size, spacing, and location of said unerupted teeth, determining actual body length percentile, body length percentile discrepancy, and concordant calorie intake based on age and theoretical body length percentile of the patient, monitoring these parameters on a serial basis, and controlling the caloric intake of the patient in accordance with the monitored parameters to effect a desired predetermined interdental spacing.

* * * * *